United States Patent
Cueni et al.

(10) Patent No.: US 6,874,354 B2
(45) Date of Patent: Apr. 5, 2005

(54) SAMPLE INJECTION VALVE FOR HIGH-PERFORMANCE LIQUID CHROMATOGRAPHY (HPLC) DEVICES

(75) Inventors: Hansjörg Cueni, Stansstad (CH); Heinrich Scherrer, Büsserach (CH)

(73) Assignee: CTC Analytics AG, Zwingen (CH)

( * ) Notice: Subject to any disclaimer, the term of this patent is extended or adjusted under 35 U.S.C. 154(b) by 148 days.

(21) Appl. No.: 10/415,872

(22) PCT Filed: Nov. 12, 2001

(86) PCT No.: PCT/CH01/00661

§ 371 (c)(1),
(2), (4) Date: May 5, 2003

(87) PCT Pub. No.: WO02/39105

PCT Pub. Date: May 16, 2002

(65) Prior Publication Data

US 2004/0020542 A1 Feb. 5, 2004

(30) Foreign Application Priority Data

Nov. 13, 2000 (CH) .............................. 2207/00

(51) Int. Cl.[7] .............................................. G01N 31/08
(52) U.S. Cl. ................... 73/61.55; 73/863.72
(58) Field of Search .................. 73/863.71, 863.72, 73/863.73, 864.83, 61.55; 137/240

(56) References Cited

U.S. PATENT DOCUMENTS

| 3,630,371 | A | | 12/1971 | Hrdina |
| 4,444,066 | A | | 4/1984 | Ogle et al. |
| 4,811,611 | A | | 3/1989 | Uffenheimer |
| 5,194,226 | A | | 3/1993 | Tomoff et al. |
| 5,308,774 | A | | 5/1994 | Miura et al. |
| 6,012,487 | A | * | 1/2000 | Hauck .................... 137/625.11 |
| 6,260,407 | B1 | * | 7/2001 | Petro et al. ................. 73/61.52 |

FOREIGN PATENT DOCUMENTS

EP 0360604 3/1990

* cited by examiner

*Primary Examiner*—John Fox
(74) *Attorney, Agent, or Firm*—Ladas & Parry LLP

(57) ABSTRACT

The sample injection valve for high-performance liquid chromatography (HPLC) devices comprises a stator with inlets for the sample and the mobile phase, outlets leading to the chromatography column and to a waste collector, as well as connections for both ends of a sample loop. Its rotor has the customary connection channels. An additional washing liquid inlet (7) opens into the connecting channel (9) that, in one valve position, connects the sample inlet (1) to the outlet (2) leading to the waste collector. This enables the sample inlet and the pipette or syringe located therein to be rinsed.

2 Claims, 1 Drawing Sheet

SAMPLE INJECTION VALVE FOR HIGH-PERFORMANCE LIQUID CHROMATOGRAPHY (HPLC) DEVICES

The invention relates to a sample injection valve for HPLC devices which comprises a stator with inlets for the sample and the mobile phase, outlets leading to the chromatography column and to a waste collector, as well as terminals for both ends of a sample loop, and a rotor with connection channels.

Sample injection valves of this type are in use in the majority of known HPLC devices. The rotor has two possible positions. In one position the sample inlet is connected to one end of the sample loop so that the latter is filled with sample. In the second position the sample inlet is normally connected to the waste collector for disposal of the remaining sample that is not required. At the same time, in the second position the sample loop is switched between the inlet for the mobile phase and the outlet leading to the column. This second position of the rotor thus corresponds to the sample injection phase, in which the quantity of sample measured into the loop is transported to the column.

The sample injection phase is utilized for cleaning the tip of the sample pipette in order to avoid contamination between successive samples. For this purpose the pipette is conventionally transferred to a separate cleaning device before being made available for collection of the next sample.

Although this method ensures that the tip is cleaned, no cleaning takes place in the inlet region on the stator, which conventionally is a type of sleeve that tightly envelops the tip during injection of the sample. Increasing accuracy of measurement has revealed that there is indeed contamination in this region.

A further disadvantage of the known method is that the cleaning processes require more time than injection of the sample, so cleaning represents a limiting factor for the sample throughput per unit time.

The object of the invention is therefore to effect the cleaning of the pipette tip and sample inlet more reliably and more rapidly.

This object is achieved according to the invention by a sample injection valve of the type mentioned at the outset, in which provision is made for an additional washing liquid inlet that, in one valve position, in which the sample inlet is connected via a connection channel to the outlet leading to the waste collector, opens into said connection channel.

Figure 1:
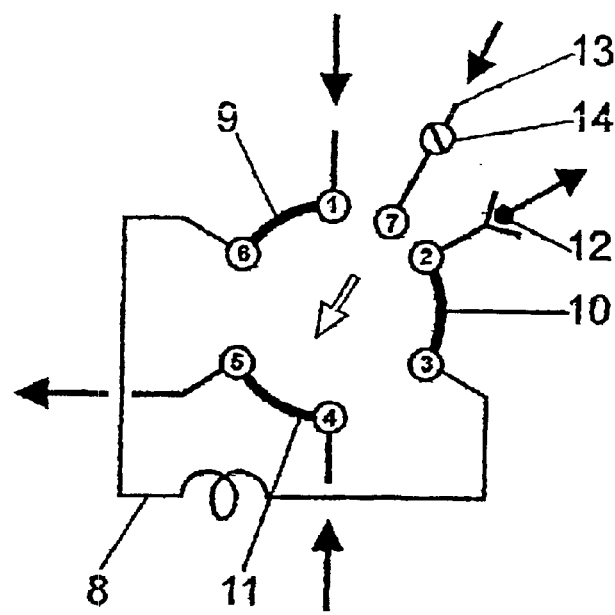
Figure 2:
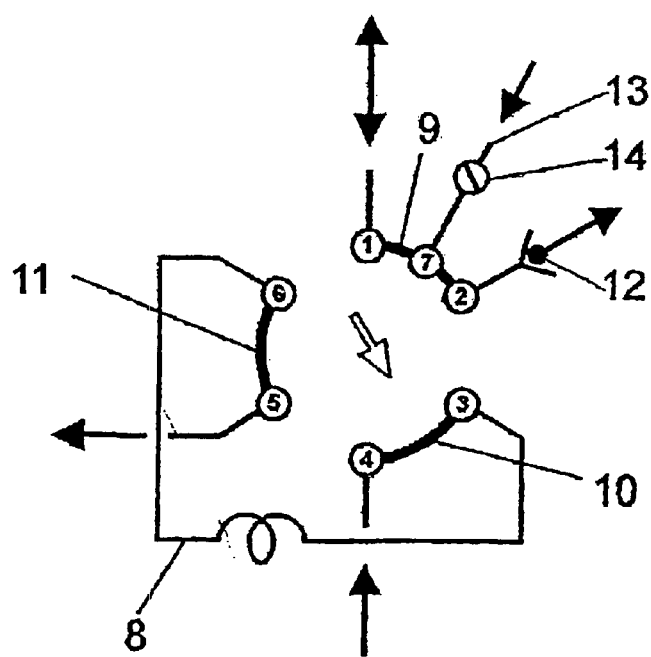

An embodiment of the invention is described below with the aid of the attached drawings, in which:

FIG. 1 is a schematic representation of a sample injection valve in one switching position, and FIG. 2 shows the sample injection valve in its second position.

Both Figures schematically show the terminals and their connections. The external shape of the sample injection valve is not shown because it is irrelevant to its function and the possible shapes of such sample injection valves are sufficiently well known.

The sample injection valve shown in the Figures has the following seven terminals on the stator: a sample inlet 1, a waste outlet 2, a terminal 3 for one end of a sample loop 8, a mobile phase inlet 4, a column terminal 5, a terminal 6 for the other end of the sample loop 8, and a washing liquid inlet 7 arranged between the sample inlet 1 and the waste outlet 2. The terminals are interconnected in different combinations via connection channels in the rotor.

The connection channels in the rotor are formed by grooves in one of the flat faces of the rotor. In the present embodiment the rotor has three grooves 9, 10 and 11. The rotor is switched between two positions to create the following connections:

In the position shown in FIG. 1 the sample inlet is connected via the groove 9 to one end of the sample loop, the other end being connected via the groove 10 to the waste outlet 2. The groove 11 connects the mobile phase inlet 4 to the column terminal. In this position the sample loop is filled with sample by means of a pipette tip or syringe needle inserted in the sample inlet, any excess running into the waste. At the same time the column is rinsed with mobile phase. The washing liquid inlet 7 is closed.

In the position shown in FIG. 2 the sample inlet 1 is connected via the groove 9 to the washing liquid inlet 7 and the waste outlet 2. At the same time the groove 10 connects one end 3 of the sample loop 8 to the mobile phase inlet 4 and the groove 11 connects the other end 6 of the sample loop 8 to the column terminal 5. The latter connection allows the quantity of sample present in the sample loop 8 to be fed into the column.

The connection of the sample inlet 1 to the washing liquid inlet 7 in the second position of the rotor, shown in FIG. 2, allows the pipette or syringe to suck up the quantity of washing liquid required for cleaning and then to discharge it into the waste. A check valve 12 is arranged in the line leading to the waste collector, directly outside the waste outlet, in order to prevent liquid flowing back from the waste into the pipette while it is being sucked up.

A feed line 13, in which a stop valve 14 is arranged, leads to the washing liquid inlet 7. Said stop valve 14 is operated for cleaning of the sample injection valve and injection syringe and is open for sucking up the washing liquid and closed for discharging it.

After this cleaning step the pipette or syringe is immediately ready for collection of the next sample. The time previously needed to transfer the pipette to the cleaning device is eliminated, thereby markedly increasing the sample throughput rate.

What is claimed is:

1. Sample injection valve for HPLC devices which comprises a stator with inlets for the sample and the mobile phase, outlets leading to the chromatography column and to a waste collector, as well as terminals for both ends of a sample loop, and a rotor with connection channels, characterized in that provision is made for an additional washing liquid inlet (7) that, in one valve position, in which the sample inlet (1) is connected via a connection channel (9) to the outlet (2) leading to the waste collector, opens into said connection channel.

2. Sample injection valve according to claim 1, characterized by a check valve (12) at the outlet (2) leading to the waste collector.

* * * * *